(12) United States Patent
Garg

(10) Patent No.: US 9,864,730 B2
(45) Date of Patent: Jan. 9, 2018

(54) THERMAL AWARE HEADPHONES

(71) Applicant: QUALCOMM Incorporated, San Diego, CA (US)

(72) Inventor: Dinesh K. Garg, San Diego, CA (US)

(73) Assignee: QUALCOMM Incorporated, San Diego, CA (US)

(*) Notice: Subject to any disclaimer, the term of this patent is extended or adjusted under 35 U.S.C. 154(b) by 54 days.

(21) Appl. No.: 13/769,214

(22) Filed: Feb. 15, 2013

(65) Prior Publication Data

US 2014/0129010 A1    May 8, 2014

Related U.S. Application Data

(60) Provisional application No. 61/722,747, filed on Nov. 5, 2012.

(51) Int. Cl.
| | | |
|---|---|---|
| G06F 17/00 | (2006.01) | |
| H04R 1/10 | (2006.01) | |
| A61B 5/00 | (2006.01) | |
| A61B 5/01 | (2006.01) | |
| H04M 1/05 | (2006.01) | |
| H04M 1/60 | (2006.01) | |
| H04M 1/725 | (2006.01) | |

(52) U.S. Cl.
CPC ........... *G06F 17/00* (2013.01); *H04R 1/1016* (2013.01); *A61B 5/0008* (2013.01); *A61B 5/01* (2013.01); *A61B 5/6817* (2013.01); *H04M 1/05* (2013.01); *H04M 1/6066* (2013.01); *H04M 1/72558* (2013.01); *H04M 2250/12* (2013.01); *H04R 2420/07* (2013.01)

(58) Field of Classification Search
CPC ........... A61B 5/4094; A61B 5/18; A61B 5/01; A61B 2560/0242; A61B 5/0008; A61B 5/0878; A61B 2017/00084; A61B 2017/00132; A61B 2019/465; A61B 2560/0252; A61B 2562/0271; A61B 5/0002; A61N 1/37
See application file for complete search history.

(56) References Cited

U.S. PATENT DOCUMENTS

| | | | |
|---|---|---|---|
| 4,652,915 A | | 3/1987 | Heller, III |
| 6,059,733 A | * | 5/2000 | Brune .................. A01K 11/007 128/899 |
| 8,441,356 B1 | * | 5/2013 | Tedesco et al. ............ 340/573.1 |

(Continued)

OTHER PUBLICATIONS

International Search Report and Written Opinion—PCT/US2013/068593, International Search Authority—European Patent Office, dated Feb. 10, 2014.

*Primary Examiner* — Jingge Wu
(74) *Attorney, Agent, or Firm* — Arent Fox, LLP and Qualcomm Incorporated

(57) ABSTRACT

A method, an apparatus, and a computer program product are provided. The apparatus obtains a measure of a mammalian body temperature. The measure is based on at least one body temperature sensed at a second device remote from a first device. The apparatus concludes a criterion is satisfied when the measure is less than a first threshold corresponding to an expected body temperature and the measure approaches a second threshold corresponding to an ambient temperature. The apparatus initiates a control of the first user device when the criterion is satisfied.

36 Claims, 15 Drawing Sheets

(56) References Cited

U.S. PATENT DOCUMENTS

| | | |
|---|---|---|
| 8,461,981 B1* | 6/2013 | Spector .................... 340/539.12 |
| 2001/0044588 A1 | 11/2001 | Mault |
| 2004/0026409 A1* | 2/2004 | Bikhovsky .................... 219/527 |
| 2006/0025820 A1* | 2/2006 | Phillips et al. .................... 607/2 |
| 2006/0045304 A1 | 3/2006 | Lee et al. |
| 2006/0229531 A1* | 10/2006 | Goldberger et al. ......... 600/573 |
| 2007/0297618 A1 | 12/2007 | Nurmi et al. |
| 2008/0064992 A1* | 3/2008 | Stewart et al. .................... 601/7 |
| 2008/0266118 A1* | 10/2008 | Pierson et al. ............. 340/573.6 |
| 2008/0281411 A1* | 11/2008 | Berreklouw ................. 623/2.11 |
| 2008/0297336 A1* | 12/2008 | Lee ................ 340/439 |
| 2009/0010461 A1 | 1/2009 | Klinghult et al. |
| 2009/0105605 A1* | 4/2009 | Abreu .................. A61B 5/0008 600/549 |
| 2009/0124286 A1 | 5/2009 | Hellfalk et al. |
| 2009/0215439 A1 | 8/2009 | Hamilton et al. |
| 2010/0268105 A1* | 10/2010 | Feldman ............. A61B 5/0803 600/529 |
| 2010/0303258 A1 | 12/2010 | Pan |
| 2011/0140913 A1* | 6/2011 | Montenero ............. 340/870.07 |
| 2011/0160964 A1* | 6/2011 | Obradovich .................... 701/41 |
| 2012/0012297 A1* | 1/2012 | Nakagawa et al. ........... 165/247 |
| 2012/0156933 A1 | 6/2012 | Kreger et al. |
| 2012/0313746 A1* | 12/2012 | Rahman et al. ............... 340/5.1 |
| 2013/0053099 A1* | 2/2013 | Nabata et al. ............. 455/556.1 |
| 2013/0144130 A1* | 6/2013 | Russell et al. ................ 600/301 |
| 2013/0158376 A1* | 6/2013 | Hayter et al. ................ 600/347 |
| 2013/0158713 A1* | 6/2013 | Geissler et al. ............. 700/275 |
| 2013/0166079 A1* | 6/2013 | Wilhelm et al. ............. 700/282 |
| 2014/0156085 A1* | 6/2014 | Modi et al. .................. 700/276 |

* cited by examiner

THERMAL AWARE HEADPHONES

CROSS-REFERENCE TO RELATED APPLICATIONS

The present application claims priority to U.S. Provisional Application No. 61/722,747 filed Nov. 5, 2012, which is hereby incorporated by reference herein.

BACKGROUND

Field

The present disclosure relates generally to mechanisms for controlling user devices, and more particularly, to temperature based control of media players.

Background

Conventional media player systems, including media players resident in computing devices, such as laptops and desktops, and mobile devices such as Smartphones, tablets and MP3 players, and accompanying auditory devices, such as earphones or headphones, operate through manual activation of control buttons. Often, a user of such systems removes the auditory device from himself without manually activating control buttons so as to stop or pause the media player. As a result, the media player continues to play, thereby inconveniencing the user through loss of place of the current media, and wasting resources including device power and network bandwidth.

SUMMARY

In an aspect of the disclosure, a method, a computer program product, and an apparatus are provided for controlling a first user device having a media player. The apparatus processes a mammalian body temperature relative to a temperature criterion. The body temperature may be sensed at a second user device, e.g., earphones, remote from the first user device. The apparatus communicates a signal to the first user device, if the criterion is satisfied. The signal is configured to initiate a control of the first user device. The apparatus processes the sensed body temperature by comparing a measure of the sensed body temperature to the criterion. The criterion may be a threshold based on an expected body temperature. In which case, the apparatus concludes the criterion is satisfied if the measure is less than the threshold. The criterion may also be a threshold based on an ambient temperature. In which case, the apparatus concludes the criterion is satisfied if the measure approaches the threshold. A measure may be deemed to approach a threshold when the measure is within a certain range of the threshold, or when the time rate of change of the measure exceeds a predetermined rate. The criterion may involve both of the foregoing thresholds, in which case, the apparatus concludes the criterion is satisfied if the measure is both less than the body-temperature threshold and approaches the ambient temperature threshold.

DETAILED DESCRIPTION

Figure 1:
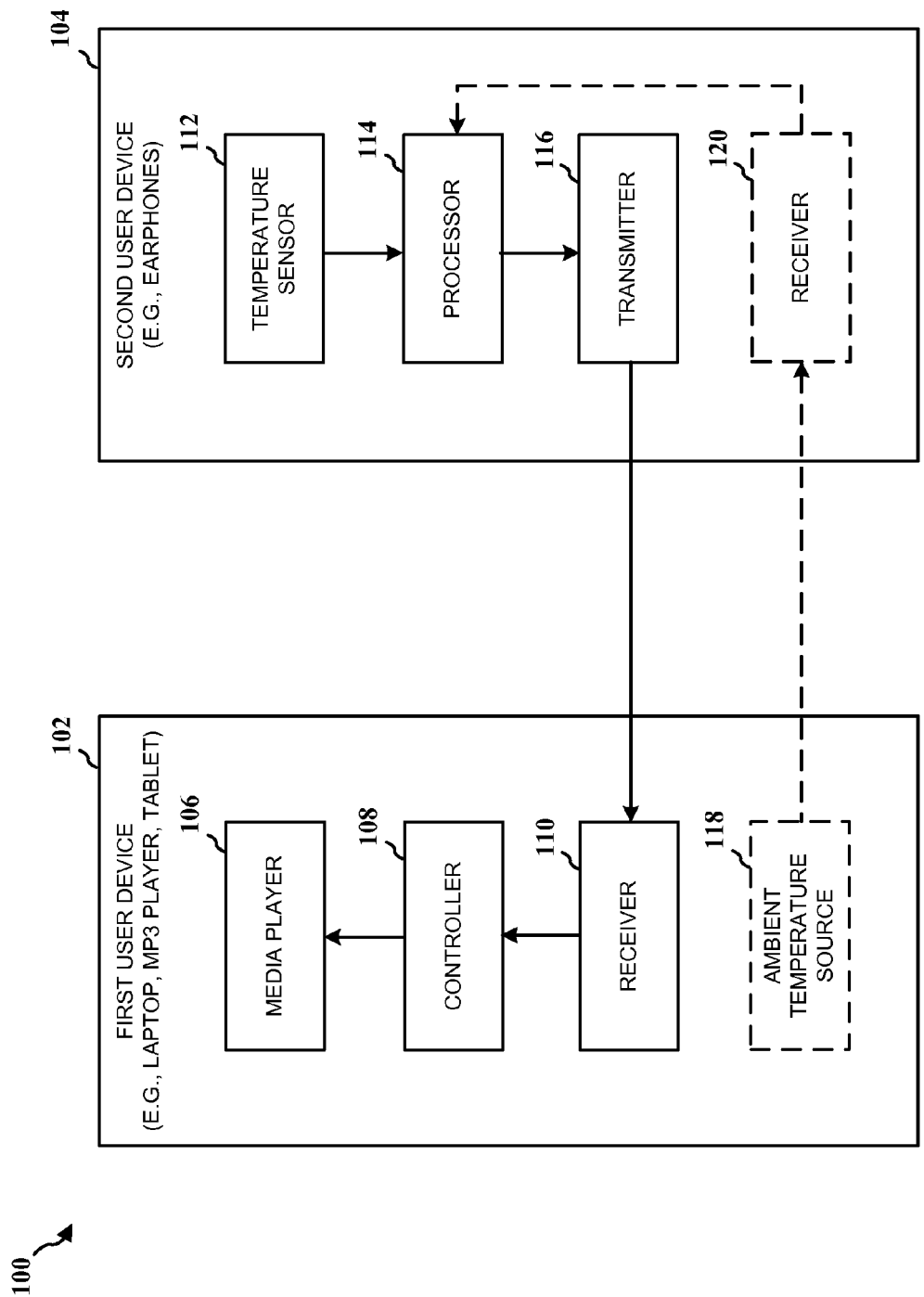
FIG. 1 is a diagram illustrating a first configuration of a user device system, wherein a second user device is configured to process temperature signals and transmit signals to a first user device for initiating control of the first user device.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Several aspects of computing systems will now be presented with reference to various apparatus and methods. These apparatus and methods will be described in the following detailed description and illustrated in the accompanying drawings by various blocks, modules, components, circuits, steps, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system.

By way of example, an element, or any portion of an element, or any combination of elements may be implemented with a "processing system" that includes one or more processors. Examples of processors include microprocessors, microcontrollers, digital signal processors (DSPs), field programmable gate arrays (FPGAs), programmable logic devices (PLDs), state machines, gated logic, discrete hardware circuits, and other suitable hardware configured to perform the various functionality described throughout this disclosure. One or more processors in the processing system may execute software. Software shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

Accordingly, in one or more exemplary embodiments, the functions described may be implemented in hardware, software, firmware, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), and floppy disk where disks usually reproduce data magnetically, while discs reproduce data optically with lasers. Combinations of the above should also be included within the scope of computer-readable media.

FIG. 1 is a diagram illustrating a first configuration of a user device system 100. The system 100 includes a first user device 102 and a second user device 104. The first user device 102 may be a desktop computer, a laptop computer, a Smartphone, a MP3 player, or any other similar device having media player capability. The first user device 102 includes a media player 106 for playing music and/or video content, a controller 108 for controlling operation of the media player 106, and a receiver 110 for receiving signals from the second user device 104. The first user device 102 may also include an ambient temperature source 118.

The second user device 104 may be an auditory device such as headphones or earphones, or a visual device such as augmented reality (AR) glasses or 3D glasses. The second user device 104 includes a temperature sensor 112 for sensing temperatures and outputting corresponding signals, and a processor 114 for processing signals provided by the temperature sensor. In general terms, the processor 114 determines a measure based on the temperature signals received from the temperature sensor 112 and compares the measure to a criterion. If the criterion is satisfied by the measure, the processor 114 outputs a signal to a transmitter 116. The transmitter 116, in turn, transmits the signal to the first user device 102. The second user device 104 may also include a receiver 120 that receives ambient temperature signals from the ambient temperature source 118, and forwards them to the processor 114.

Figure 2:
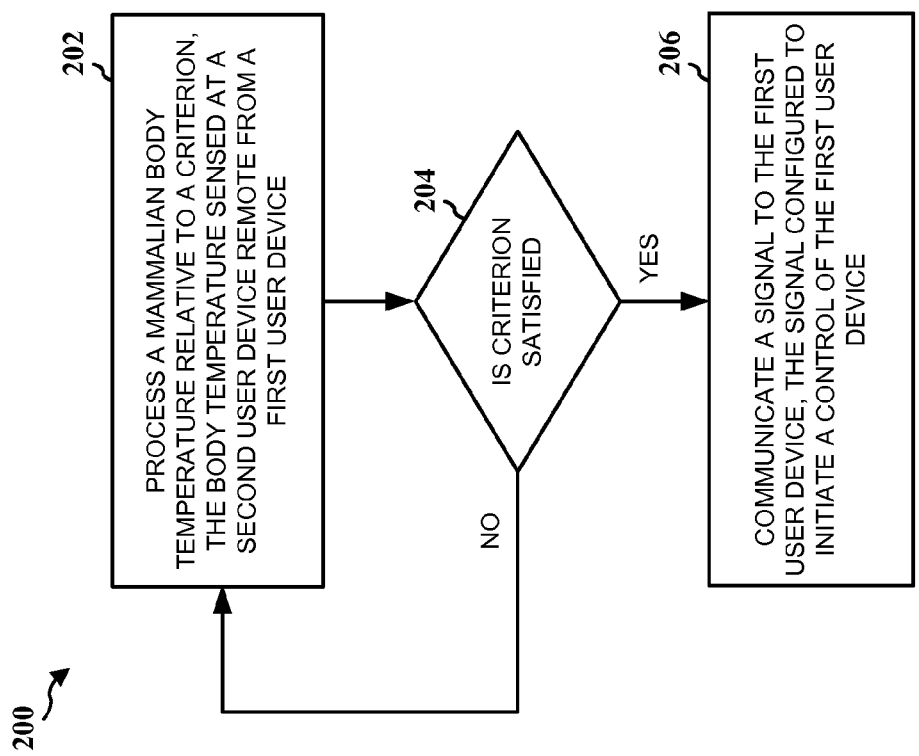
FIG. 2 is a flow chart of a method implemented by the second user device of FIG. 1.

FIG. 2 is a flow chart of a method 200 of controlling operation of the first user device of FIG. 1. The method 200 is performed by a second user device, such as earphones, headphone or glasses. The second user device includes one or more temperature sensors positioned with respect to other components of the device so as to place the sensor in contact with a part of a mammalian body. For example, a temperature sensor may be placed on one or both earpieces of an earphone set such that when worn by a user the temperature sensor is positioned adjacent body tissue within the ear to sense temperatures indicative of user body temperature. Likewise, with respect to eyeglasses, a temperature sensor may be located at an earpiece at the end of a temple such that when worn by a user the temperature sensor is positioned adjacent tissue behind the ear. The second user device may also include one or more other temperature sensors positioned with respect to other components of the device so as to place the one or more other sensors in ambient surroundings, not in contact with a part of a mammalian body to sense temperatures indicative of ambient air in the vicinity of the second user device.

At step 202, the second user device processes a mammalian body temperature relative to a temperature criterion. The body temperature is sensed at the second user device which is remote from the first user device. At step 204, the second user device determines if the criterion is satisfied. If the criterion is not satisfied, the process returns to step 202 for processing of a next body temperature. If the criterion is satisfied, then at step 206, the second user device communicates a signal to the first user device. The signal is configured to initiate a control, e.g., pause play, stop play, power down, of a media player within the first user device.

Processing the body temperature in steps 202, 204 and 206 may include comparing a measure of the temperature sensed by the temperature sensor intended to be in contact with the user, to the criterion. In one arrangement, the criterion is a threshold based on an expected body temperature and processing includes concluding the criterion is satisfied if the measure is less than the threshold. In a basic form, the measure is the current sensed temperature and the threshold is a temperature corresponding to a temperature indicative of contact between the temperature sensor and body tissue. A drop in current sensed temperature below the threshold essentially indicates that the temperature sensors are no longer adjacent body tissue, which in turn indicates that the user of second user device, e.g., earphones, is no longer wearing the device. Accordingly, playing of the media player is paused or stopped. The foregoing threshold temperature may be set at a certain amount below an average body temperature, wherein the average body temperature is standard among all users, e.g., 98.7 degrees F., or is individually set for each user. For example, the threshold may be set at 3 degrees F. below body temperature. In the case of individually set average body temperatures, the processor monitors the sensed temperatures over a period of time during which the user is known to be wearing the second user device and calculates an individualized average body temperature based on the sensed temperatures.

In another arrangement, the criterion may be a threshold based on an ambient temperature and processing includes concluding the criterion is satisfied if the measure approaches or drifts toward the threshold. In a basic form, the measure is the current temperature sensed and the threshold is a temperature corresponding to the ambient temperature in the vicinity of the user. In one configuration, the ambient temperature is provided by one or more temperature sensors positioned on the second user device so as to place the sensors in ambient surroundings, not in contact with a part of a mammalian body. Alternatively, or in addition, ambient temperature measurements may be obtained from a source remote from the second user device, such as an ambient temperature source 118 (FIG. 1) associated with the first user device. The ambient temperature source 118 may be one or more of a temperature sensor on the first user device, or a first-user-device interface that allows the user to input a temperature, or a temperature application resident in the first user device that obtains temperatures from remote sources, e.g., another device in the vicinity of the first user device or a location based temperature content provider, or any other similar temperature acquisition means. Ambient temperature measurements from the ambient temperature source 118 are provided to the second user device by the first user device periodically, either through a wireless or wired interface.

In order to avoid spurious false conclusions that the criterion is not satisfied, leading to unwanted stopping of the media player, the process may invoke other operations. For example, the measure of sensed temperatures may be a running average of sensed temperatures, as opposed to a single temperature. In this case, the running average is compared to the threshold so as to avoid any single, potentially erroneous temperature from triggering a media player stop. Alternatively, or in addition, the process may invoke a time element when concluding a criterion is not satisfied. For example, in the case of a criterion based on expected body temperature, the criterion may be deemed not satisfied when the measure of sensed temperatures is consistently below the threshold for a period of time, e.g., 5 seconds. In the case of a criterion based on ambient temperature, the criterion may be deemed not satisfied when the measure of sensed temperatures falls below the threshold and remains below the threshold for a period of time, e.g., 5 seconds, or exhibits a consistent downward trend over a period of time, e.g., 5 seconds, toward the ambient temperature threshold.

With respect to the criterion thresholds, these thresholds may be based on running averages of temperatures from one or more temperature sensors. For example, in the case of a single threshold temperature sensor, the threshold would be based on a running average of measurements from that single sensor. In the case of multiple threshold temperature sensors, the threshold may be based on an average measurement across the multiple sensors. These multiple sensors may include, for example, in the case of an expected-body-temperature criterion threshold, multiple appropriately positioned sensors on the second device. In the case of an ambient-temperature criterion threshold, these multiple sensors may include, for example, one or more appropriately positioned sensors on the second device, one or more sensors on the first user device or one or more external sources of temperature measurements, e.g., device applications or user input settings. Appropriately positioned sensors with respect to expected-body-temperature measurements correspond to sensors placed so as to be in contact with the user's body tissue during media playing. Appropriately positioned sensors with respect to ambient temperature measurements correspond to sensors placed so as to be in the vicinity of the user, but not in contact with the user's body tissue, during media playing.

As an additional operation to avoid false conclusions of criterion threshold crossing, the process of FIG. 2, may include multiple, different criterion threshold checks. For example, a measure of current sensed temperature may be checked against a first criterion threshold that is based on expected body temperatures. If the criterion is satisfied, i.e., the current sensed temperature is below the first threshold, the same measure of current sensed temperatures may be checked against a second criterion threshold that is based on ambient temperatures provided by an ambient temperature source. If the second criterion threshold is satisfied, i.e., the current sensed temperature is approaching the second threshold, the conclusion of criterion threshold crossing is confirmed and control of the media player is executed accordingly. A sensed temperature may be deemed to approach the second threshold when the temperature is within a certain range of the threshold, or when the time rate of change of the temperature exceeds a predetermined rate.

As yet another additional operation, in the case of multiple sources of ambient temperature measurements, the veracity of measurements provided by a first source, e.g., sensors on the second under device, may be confirmed by measurements provided by a second source, e.g., a first-user-device ambient temperature source. If the two measurements are not sufficiently similar, the measurement provided by the first source may be deemed inaccurate and ignored for purposes of media player control processing. A determination of whether measurements are sufficiently similar may be based on a degree of closeness, for example, two temperatures within 3 degrees of each other may be deemed similar. Second source temperature measurements from the first user device may be provided to the second user device through wireless or wired transmission.

Figure 3:
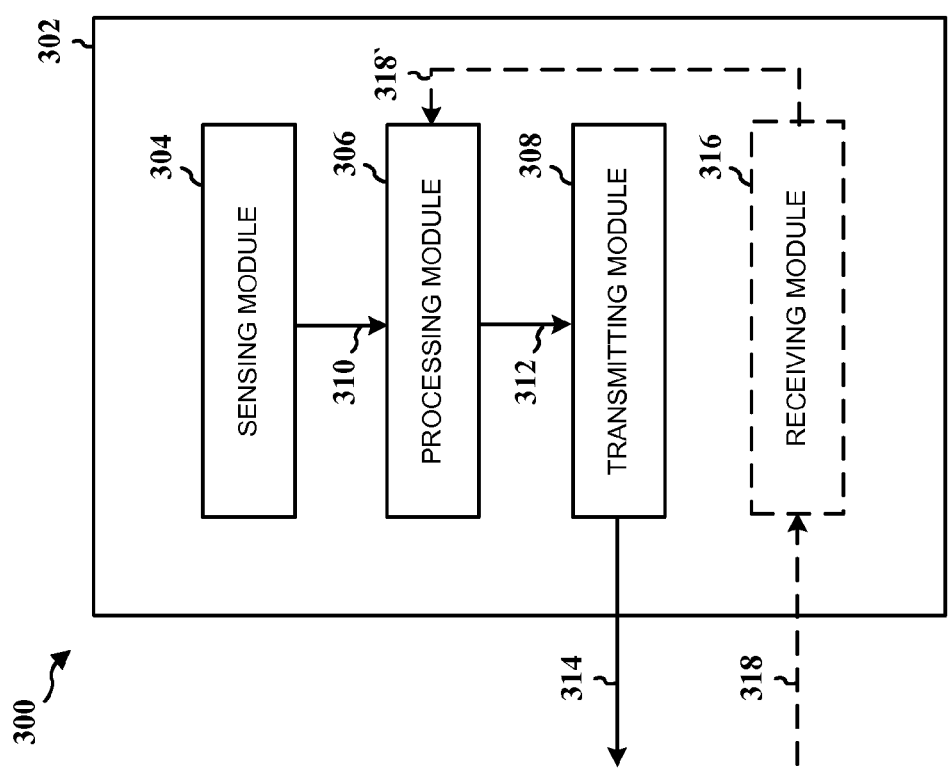
FIG. 3 is a conceptual data flow diagram illustrating the data flow between different modules/means/components in an apparatus corresponding to the second user device of FIG. 1.

FIG. 3 is a conceptual data flow diagram 300 illustrating the data flow between different modules/means/components in an exemplary apparatus 302, e.g., a second user device, configured to implement the process of the flow chart of FIG. 2. The apparatus 302 may be an auditory device, such as earphones, headphone or a visual device, such as glasses. The apparatus 302 includes a sensing module 304 that senses body temperature and outputs corresponding temperature signals 310 and a processing module 306 that processes the temperature signals to potentially produce a trigger signal 312. The apparatus 302 further includes a transmitting module 308 that receives the trigger signal 312 and generates a control signal 314 that includes information corresponding to the trigger signal. The control signal 314 is transmitted to a first user device, e.g., a remote media player device. Signal transmission may be wireless, e.g., Bluetooth, or wired, e.g., through the earphone wire. The apparatus may further include a receiving module 316 that may receive ambient temperature measurement signals 318 from a first user device. These ambient temperature measurement signals 318' are forwarded to the processing module 306 for processing together with the temperature signals 316. In this case, the ambient temperature signals are used as described above with reference to FIG. 2, to determine whether a trigger signal 312 is output.

The apparatus 302 may include additional modules that perform each of the steps of the algorithm in the aforementioned flow chart of FIG. 2, and the further details described with respect to those steps. As such, each step in the aforementioned flow chart of FIG. 2 may be performed by a module and the apparatus may include one or more of those modules. The modules may be one or more hardware components specifically configured to carry out the stated processes/algorithm, implemented by a processor configured to perform the stated processes/algorithm, stored within a computer-readable medium for implementation by a processor, or some combination thereof.

Figure 4:
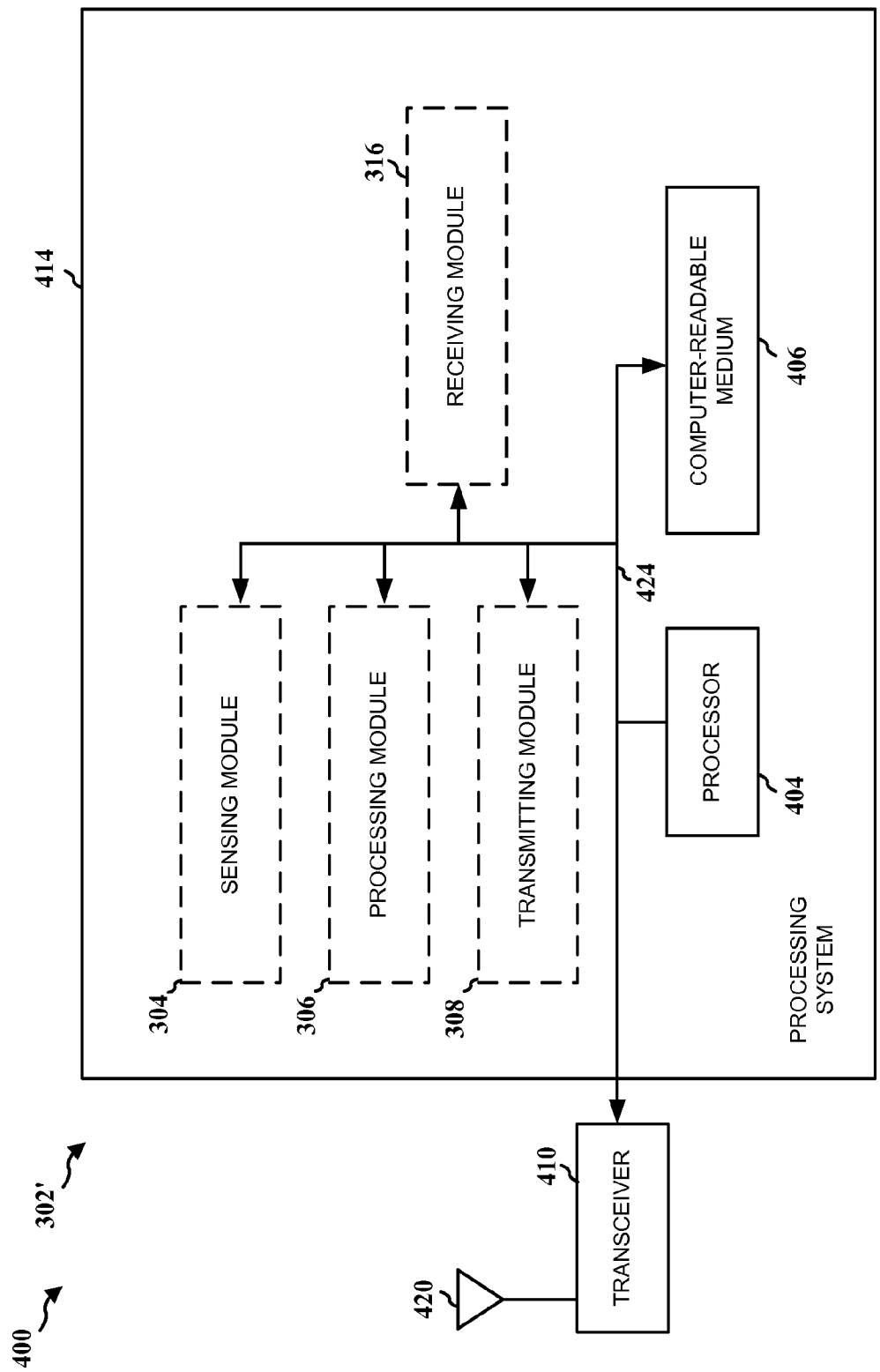
FIG. 4 is a diagram illustrating an example of a hardware implementation for an apparatus corresponding to the second user device of FIG. 1 employing a processing system.

FIG. 4 is a diagram 400 illustrating an example of a hardware implementation for an apparatus 302' employing a processing system 414. The processing system 414 may be implemented with bus architecture, represented generally by the bus 424. The bus 424 may include any number of interconnecting buses and bridges depending on the specific application of the processing system 414 and the overall design constraints. The bus 424 links together various circuits including one or more processors and/or hardware modules, represented by the processor 404, the modules 304, 306, 308, 316 and the computer-readable medium 406. The bus 424 may also link various other circuits such as timing sources, peripherals, voltage regulators, and power management circuits, which are well known in the art, and therefore, will not be described any further.

The processing system 414 may be coupled to a transceiver 410. The transceiver 410 is coupled to one or more antennas 420. The transceiver 410 provides a means for communicating with various other apparatus over a transmission medium. The transceiver 410 receives information from the processing system 414, specifically the transmitting module 308, and based on the received information, generates a signal to be applied to the one or more antennas 420. The processing system 414 includes a processor 404 coupled to a computer-readable medium 406. The processor 404 is responsible for general processing, including the execution of software stored on the computer-readable medium 406. The software, when executed by the processor 404, causes the processing system 414 to perform the various functions described supra for any particular apparatus. The computer-readable medium 406 may also be used for storing data that is manipulated by the processor 404 when executing software. The processing system further includes at least one of the modules 304, 306, 308 and 316. The modules may be software modules running in the processor 404, resident/stored in the computer readable medium 406, one or more hardware modules coupled to the processor 404, or some combination thereof.

In one configuration, the apparatus 302/302' includes means for processing a mammalian body temperature relative to a temperature criterion. The body temperature is sensed at a second user device remote from the first user device. The apparatus 302/302' also includes means for communicating a signal to the first user device. The signal is configured to initiate a control of the first user device if the criterion is satisfied. The aforementioned means may be one or more of the aforementioned modules of the apparatus 302 and/or the processing system 414 of the apparatus 302' configured to perform the functions recited by the aforementioned means.

Figure 5:
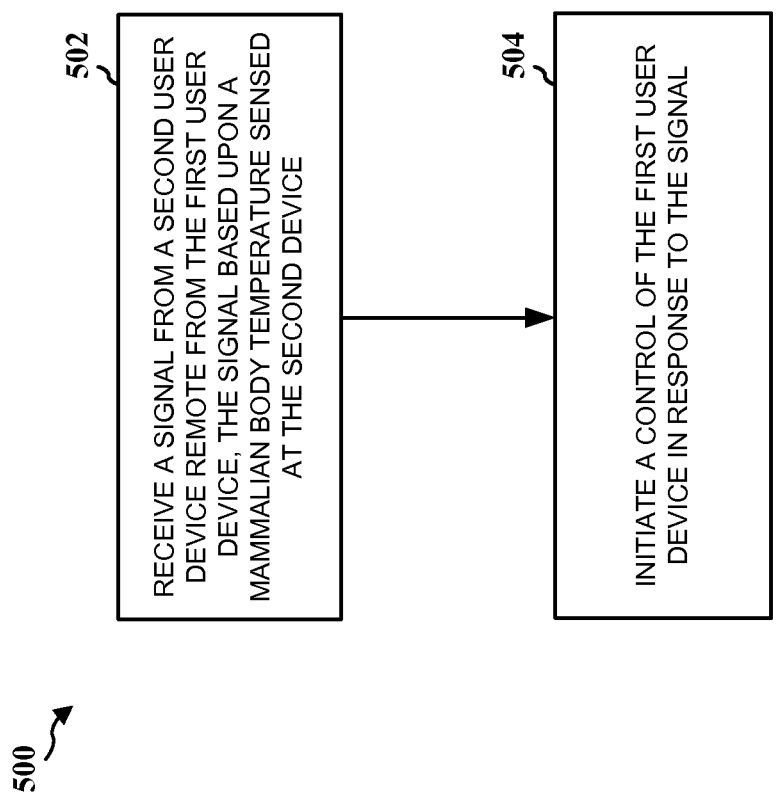
FIG. 5 is a flow chart of a method implemented by the first user device of FIG. 1.

FIG. 5 is a flow chart of a method 500 of controlling operation of the first user device of FIG. 1. The method 500 is performed by a first user device, such as a desktop computer, a laptop computer, a Smartphone, a MP3 player, or any other similar device having media player capability. At step 502, the first user device receives a signal from a second user device remote from the first user device. The second user device may be a device as described above with respect to FIG. 2. The signal is based upon a mammalian body temperature sensed at the second device. At step 504, the first user device initiates a control of the first user device in response to the signal. For example, as described above with respect to FIG. 2, a signal may be received by the first user device in cases where a measure of the current body temperature falls below an expected body-temperature threshold or drifts toward an ambient temperature threshold. In either case, the user device may stop or pause the media player.

Figure 6:
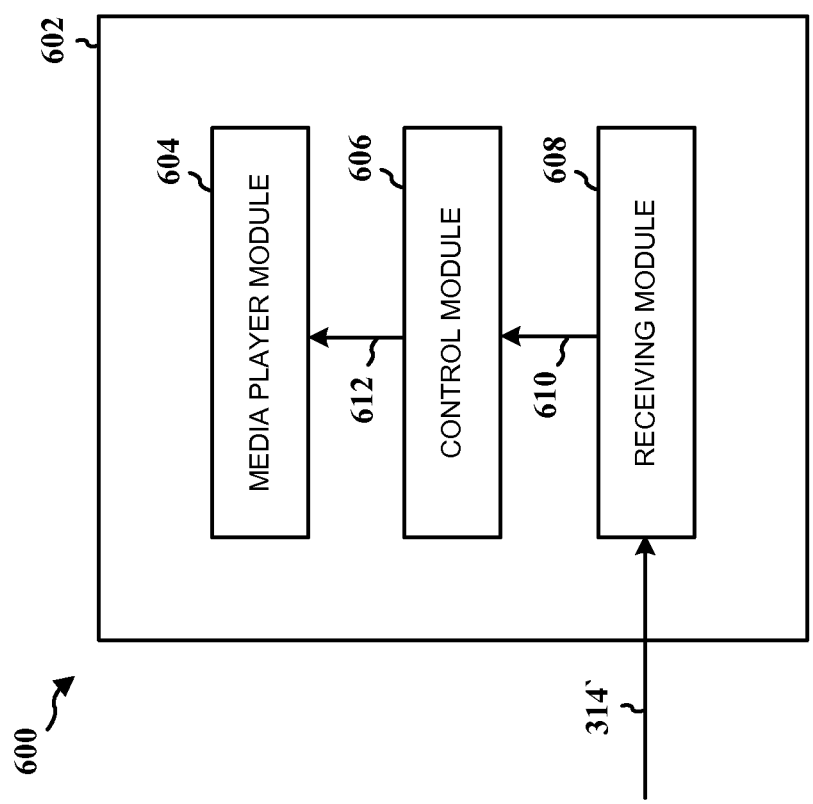
FIG. 6 is a conceptual data flow diagram illustrating the data flow between different modules/means/components in an apparatus corresponding to the first user device of FIG. 1.

FIG. 6 is a conceptual data flow diagram 600 illustrating the data flow between different modules/means/components in an exemplary apparatus 602, e.g., a first user device, configured to implement the process of the flow chart of FIG. 5. The apparatus 602 may be a desktop computer, a laptop computer, a Smartphone, a MP3 player, or any other similar device having media player capability. The apparatus 602 includes a media player module 604 that plays audio and/or video content, a control module 606 that controls operation of the media player 604, and a receiving module 608 that receives signals 314' from a remote second user device. The receiving module 608 processes the received control signal 314' as necessary and forwards a corresponding control/trigger signal 610 to the control module 606. The control module 606, in turn, processes the control/trigger signal 610 and outputs an operation control signal 612 to the media player. The operation control signal 612 effects an operation of the media player and may, for example, cause the media player to stop play, pause play or shut down.

The apparatus 602 may include additional modules that perform each of the steps of the algorithm in the aforementioned flow chart of FIG. 5, and the further details described with respect to those steps. As such, each step in the aforementioned flow chart of FIG. 5 may be performed by a module and the apparatus may include one or more of those modules. The modules may be one or more hardware components specifically configured to carry out the stated processes/algorithm, implemented by a processor configured to perform the stated processes/algorithm, stored within a computer-readable medium for implementation by a processor, or some combination thereof.

Figure 7:
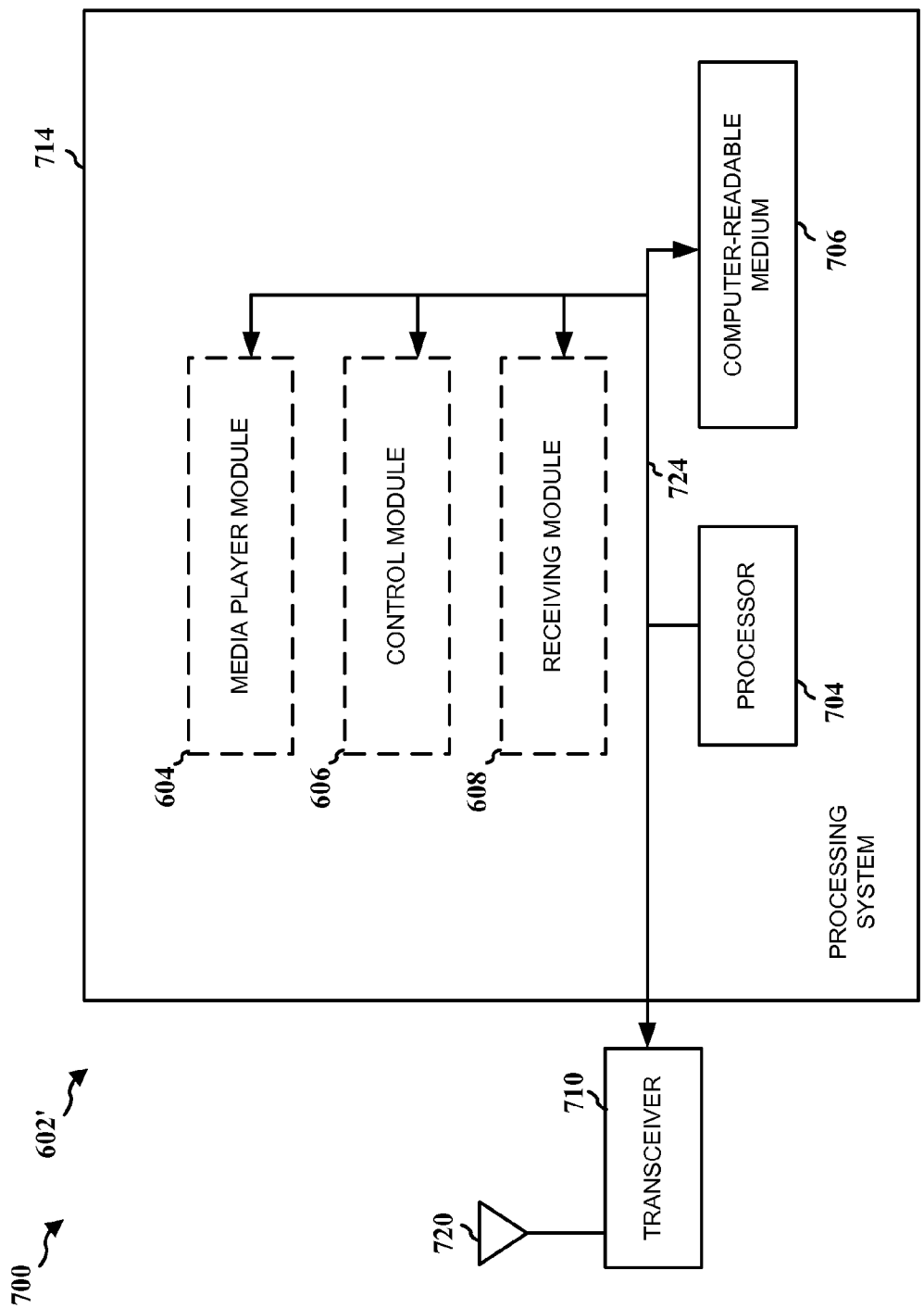
FIG. 7 is a diagram illustrating an example of a hardware implementation for an apparatus corresponding to the first user device of FIG. 1 employing a processing system.

FIG. 7 is a diagram 700 illustrating an example of a hardware implementation for an apparatus 602' employing a processing system 714. The processing system 714 may be implemented with bus architecture, represented generally by the bus 724. The bus 724 may include any number of interconnecting buses and bridges depending on the specific application of the processing system 614 and the overall design constraints. The bus 724 links together various circuits including one or more processors and/or hardware modules, represented by the processor 704, the modules 604, 606, 608, and the computer-readable medium 706. The bus 724 may also link various other circuits such as timing sources, peripherals, voltage regulators, and power management circuits, which are well known in the art, and therefore, will not be described any further.

The processing system 714 may be coupled to a transceiver 710. The transceiver 710 is coupled to one or more antennas 720. The transceiver 710 provides a means for communicating with various other apparatus over a transmission medium. The transceiver 710 receives a signal from the one or more antennas 720, extracts information from the received signal, and provides the extracted information to the processing system 714, specifically the receiving module 608. The processing system 714 includes a processor 704 coupled to a computer-readable medium 706. The processor 704 is responsible for general processing, including the execution of software stored on the computer-readable medium 706. The software, when executed by the processor 704, causes the processing system 714 to perform the various functions described supra for any particular apparatus. The computer-readable medium 706 may also be used for storing data that is manipulated by the processor 704 when executing software. The processing system further includes at least one of the modules 604, 606, and 608. The modules may be software modules running in the processor 704, resident/stored in the computer readable medium 706, one or more hardware modules coupled to the processor 704, or some combination thereof.

In one configuration, the apparatus 602/602' includes means for receiving a signal from a second user device remote from the first user device. The signal is based upon a mammalian body temperature sensed at the second device. The apparatus 602/602' also includes means for initiating a control of the first user device in response to the signal. The aforementioned means may be one or more of the aforementioned modules of the apparatus 602 and/or the processing system 714 of the apparatus 602' configured to perform the functions recited by the aforementioned means.

Figure 8:
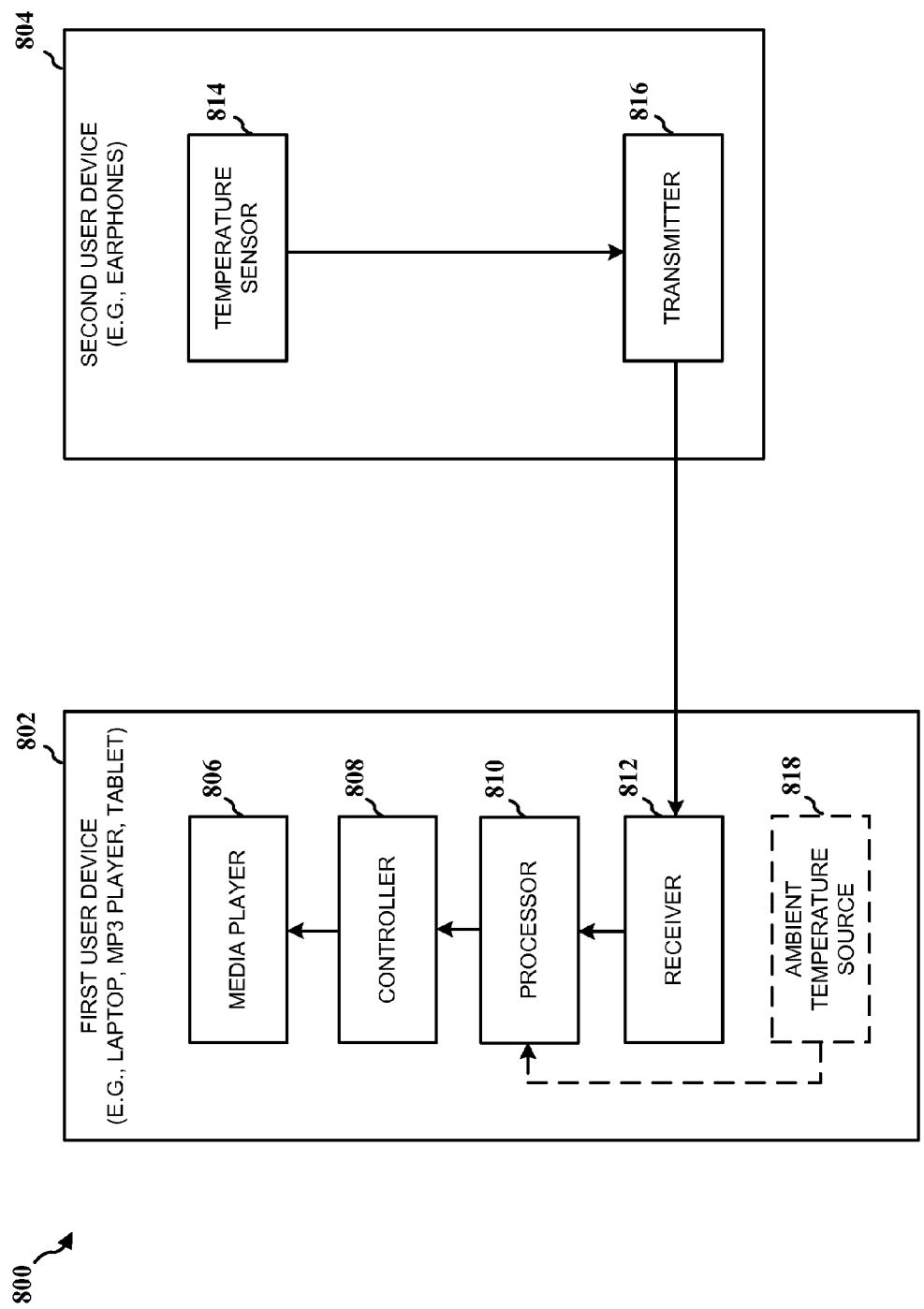
FIG. 8 is a diagram illustrating another configuration of a user device system, wherein a second user device is configured to sense and transmit temperature signals to a first user device for processing and control of the first user device.

FIG. 8 is a diagram illustrating a second configuration of a user device system 800. The system 800 includes a first user device 802 and a second user device 804. This system 800 is similar to the system of FIG. 1, except that the temperature signal processing function coexists with the media player in the first user device 802. The first user device 802 may be a desktop computer, a laptop computer, a Smartphone, a MP3 player, or any other similar device having media player capability. The first user device 802 includes a media player 806 for playing music and/or video content, a controller 808 for controlling operation of the media player 806, a processor 810 for processing temperature signals received from the second user device, and a receiver 814 for receiving the temperature signals from the second user device 804. The first user device 802 may also include an ambient temperature source 818. The ambient temperature source 818 may be one or more of a temperature sensor on the first user device, or a first-user-device interface that allows the user to input a temperature, or a temperature application resident in the first user device that obtains temperatures from remote sources, e.g., another device in the vicinity of the first user device or a location based temperature content provider, or any other similar temperature acquisition means. Ambient temperature measurements from the ambient temperature source 818 are provided to the processor 810. The processor 810 performs the same functions as the processor 114 (FIG. 1) described above, including the processes described with respect to FIG. 2. In summary, it determines a measure based on temperature signals received from the second user device and compares the measure to one or more criterion. If the criterion is satisfied by the measure, the processor 810 outputs a control/trigger signal to the controller 808, which in turn, outputs an operation control signal to the media player 806. Signals from the ambient temperature source 818 may be used to determine whether a control/trigger signal should be output, in the same manner as described above with reference to FIG. 2.

The second user device 804 may be an auditory device such as headphones or earphones, or a visual device such as augmented reality (AR) glasses or 3D glasses. The second user device 804 includes a temperature sensor 814 that provides signals corresponding to temperatures sensed at the sensor, and a transmitter 816, that transmits temperature signals to the first user device 802.

Figure 9:
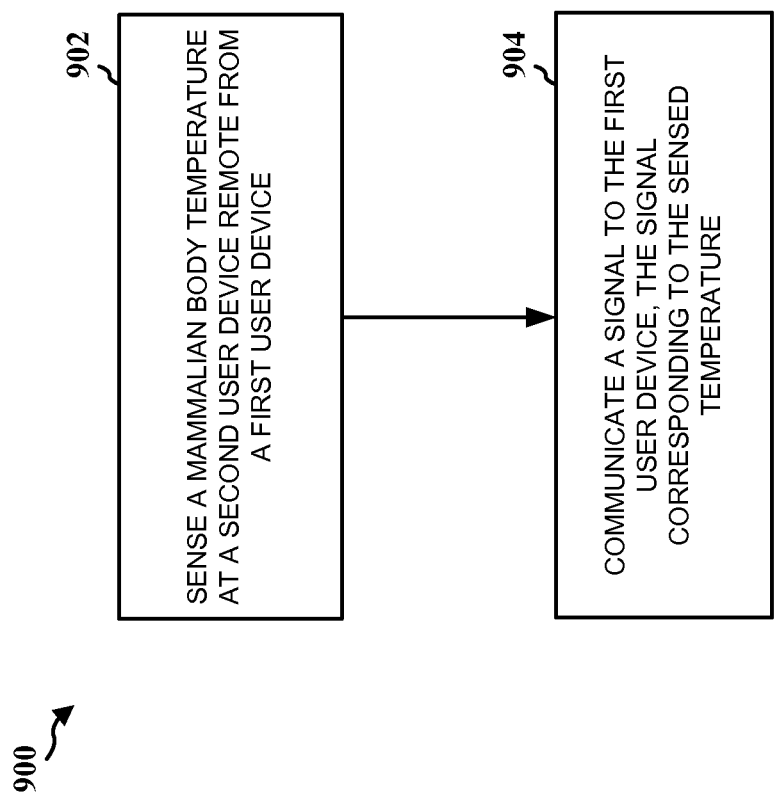
FIG. 9 is a flow chart of a method implemented by the second user device of FIG. 8.

FIG. 9 is a flow chart of a method 900 of controlling operation of the first user device of FIG. 8. The method 900 is performed by a second user device, such as earphones, headphone or glasses. At step 902, the second user device senses a mammalian body temperature at a location remote from the first user device. The temperature sensing aspects of the second user device may correspond to the temperature sensing aspects of the second user device described above with respect to FIG. 2. At step 904, the second user device communicates a signal to the first user device. The communicated signal corresponds to the sensed temperature. The temperature signals may be sensed and transmitted periodically. In one configuration, the period between signal transmissions may be a function of the amount of buffer the first user device, e.g., media player, can hold. For example, if the media player can buffer hold up to 10 seconds of content data, the transmission period may be set at half of that, or 5 seconds. Alternatively, is resources allow, the signals may be transmitted more frequently.

Figure 10:
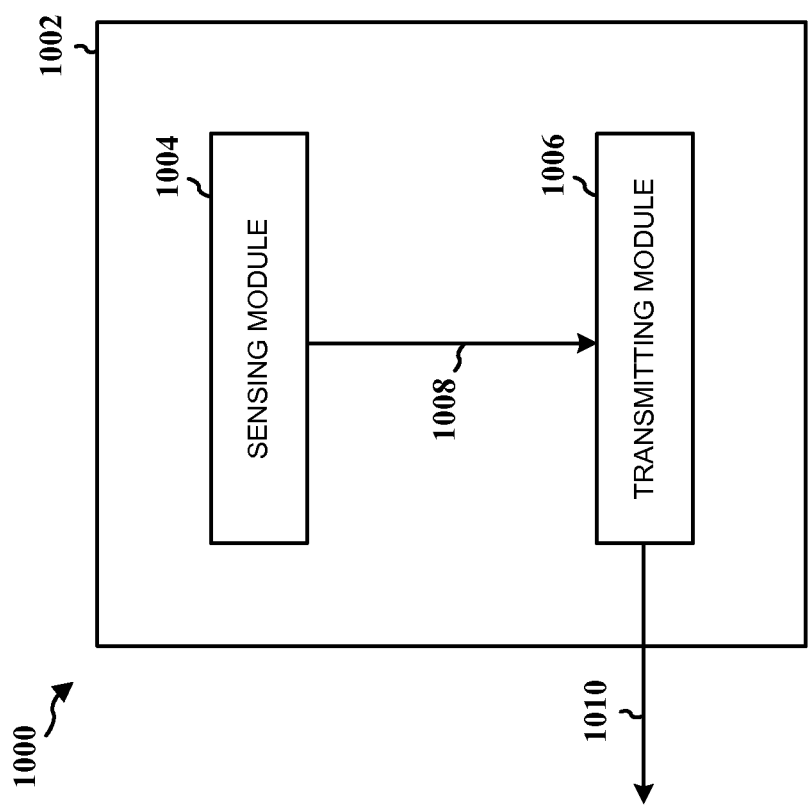
FIG. 10 is a conceptual data flow diagram illustrating the data flow between different modules/means/components in an apparatus corresponding to the second user device of FIG. 8.

FIG. 10 is a conceptual data flow diagram 1000 illustrating the data flow between different modules/means/components in an exemplary apparatus 1002, e.g., a second user device, configured to implement the process of the flow chart of FIG. 9. The apparatus 1002 may be an auditory device, such as earphones, headphone or a visual device, such as glasses. The apparatus 1002 includes a sensing module 1004 that senses body temperature and outputs corresponding sensed temperature signals 1008 and a transmitting module 1006 that transmits a temperature signal 1010 corresponding to the sensed temperature to a remote first user device, e.g., media player device.

The apparatus may include additional modules that perform each of the steps of the algorithm in the aforementioned flow chart of FIG. 9, and the further details described with respect to those steps. As such, each step in the aforementioned flow chart of FIG. 9 may be performed by a module and the apparatus may include one or more of those modules. The modules may be one or more hardware components specifically configured to carry out the stated processes/algorithm, implemented by a processor configured to perform the stated processes/algorithm, stored within a computer-readable medium for implementation by a processor, or some combination thereof.

Figure 11:
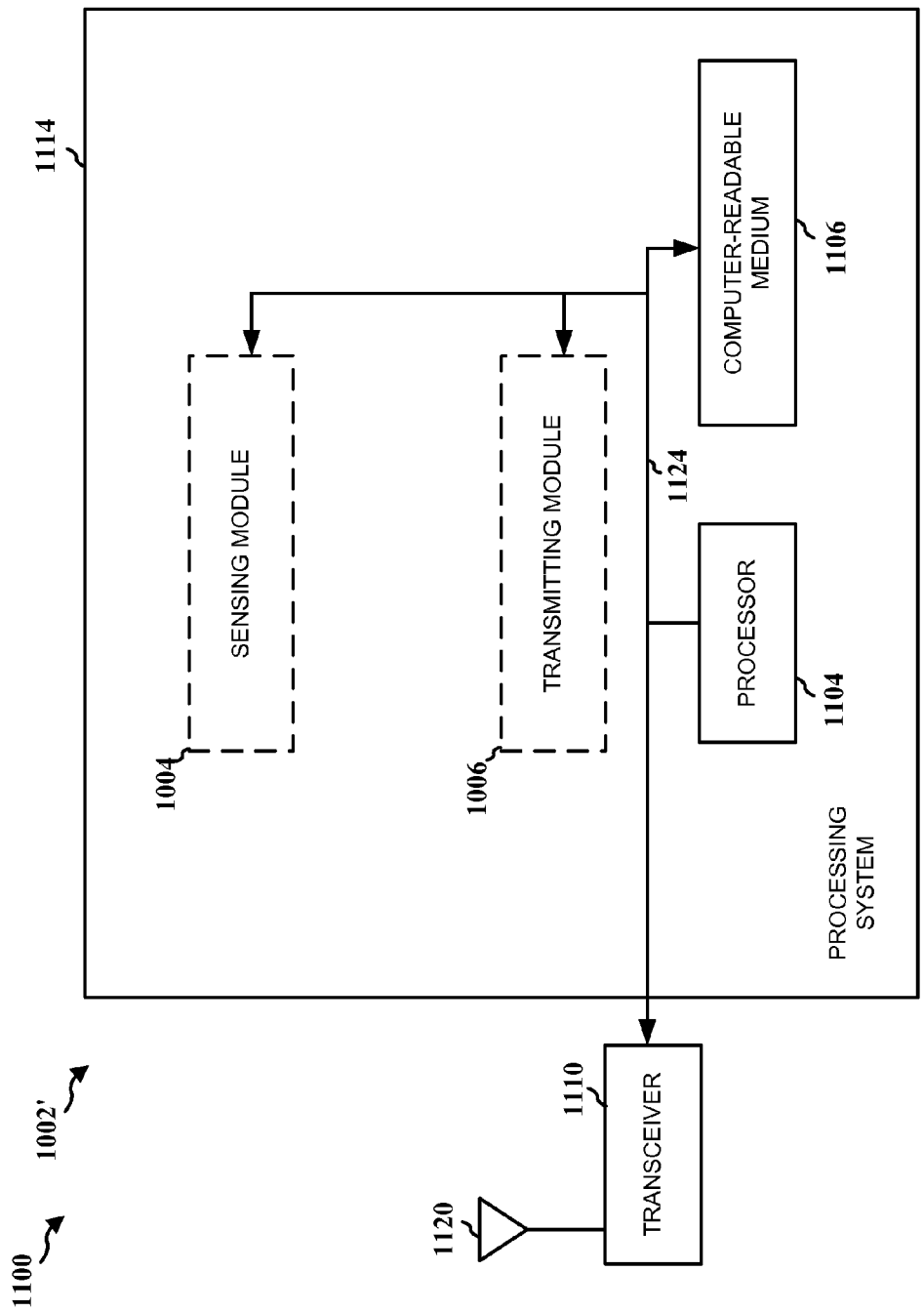
FIG. 11 is a diagram illustrating an example of a hardware implementation for an apparatus corresponding to the second user device of FIG. 8 employing a processing system.

FIG. 11 is a diagram 1100 illustrating an example of a hardware implementation for an apparatus 1002' employing a processing system 1114. The processing system 1114 may be implemented with bus architecture, represented generally by the bus 1124. The bus 1124 may include any number of interconnecting buses and bridges depending on the specific application of the processing system 414 and the overall design constraints. The bus 1124 links together various circuits including one or more processors and/or hardware modules, represented by the processor 1104, the modules 1004, 1006 and the computer-readable medium 1106. The bus 1124 may also link various other circuits such as timing sources, peripherals, voltage regulators, and power management circuits, which are well known in the art, and therefore, will not be described any further.

The processing system 1114 may be coupled to a transceiver 1110. The transceiver 1110 is coupled to one or more antennas 1120. The transceiver 1110 provides a means for communicating with various other apparatus over a transmission medium. The transceiver 1110 receives information from the processing system 1114, specifically the transmission module 1006, and based on the received information, generates a signal to be applied to the one or more antennas 1120. The processing system 1114 includes a processor 1104 coupled to a computer-readable medium 1106. The processor 1104 is responsible for general processing, including the execution of software stored on the computer-readable medium 1106. The software, when executed by the processor 1104, causes the processing system 1114 to perform the various functions described supra for any particular apparatus. The computer-readable medium 1106 may also be used for storing data that is manipulated by the processor 1104 when executing software. The processing system further includes at least one of the modules 1004 and 1006. The modules may be software modules running in the processor 1104, resident/stored in the computer readable medium 1106, one or more hardware modules coupled to the processor 1104, or some combination thereof.

In one configuration, the apparatus 1002/1002' includes means for sensing a mammalian body temperature at a second user device remote from the first user device, and means for communicating a signal to the first user device. The signal corresponds to the sensed temperature. The aforementioned means may be one or more of the aforementioned modules of the apparatus 1002 and/or the processing system 1114 of the apparatus 1002' configured to perform the functions recited by the aforementioned means.

Figure 12:
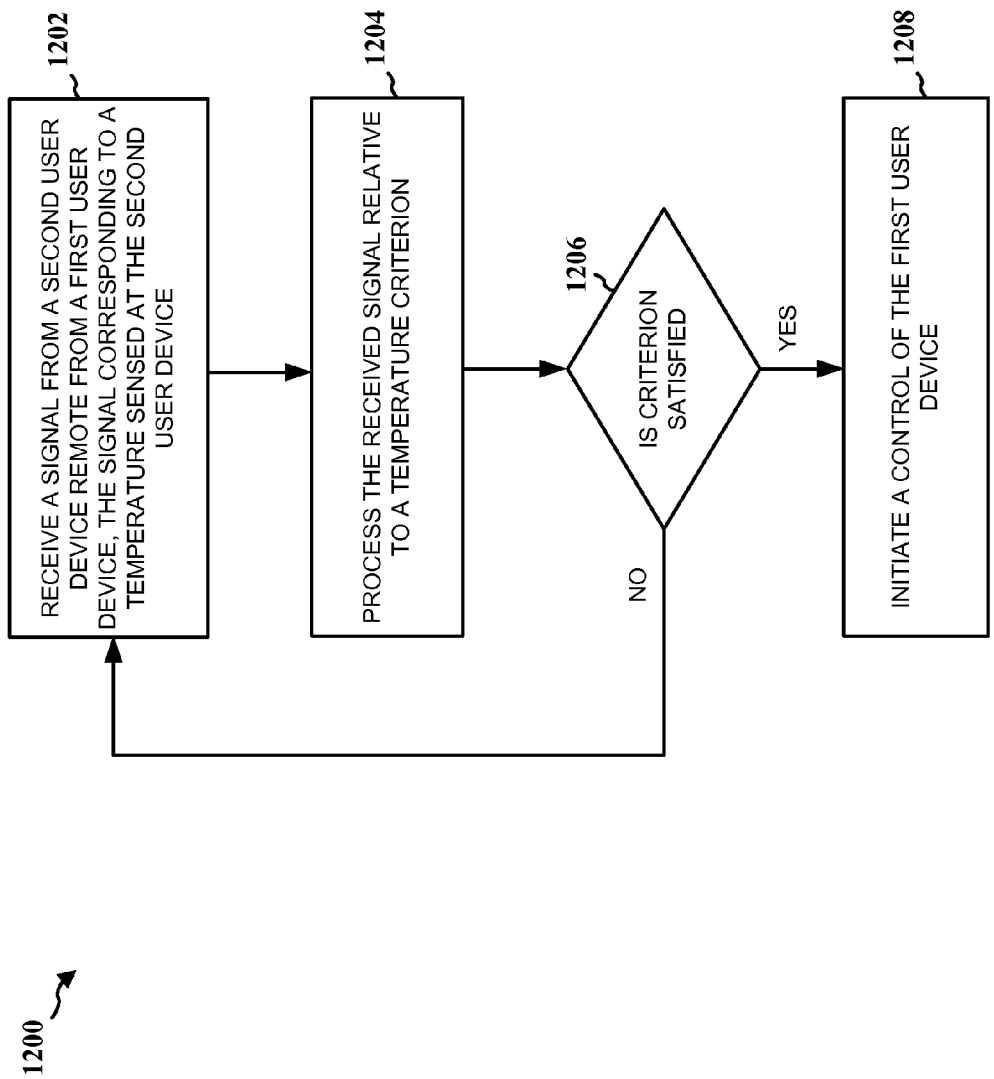
FIG. 12 is a flow chart of a method implemented by the first user device of FIG. 8.

FIG. 12 is a flow chart of a method 1200 of controlling operation of the first user device of FIG. 8. The method 1200 is performed by a first user device, such as the desktop computer, a laptop computer, a Smartphone, a MP3 player, or any other similar device having media player capability. At step 1202, the first user device receives a signal from a second user device remote from the first user device. The signal corresponds to a temperature sensed at the second user device. At step 1204, the first user device processes the received signal relative to a temperature criterion. At step 1206, the first user device determines if the criterion is satisfied. If the criterion is not satisfied, the process returns to step 1202. If the criterion is satisfied, then at step 1208, the first user device initiates a control of a media player.

The processes of steps 1204 and 1206 performed by the first user device are similar to the processes of steps 202 and 204 of FIG. 2 performed by the second user device, as described above. As such, the details of the processes of steps 1204 and 1206 are not repeated here.

Figure 13:
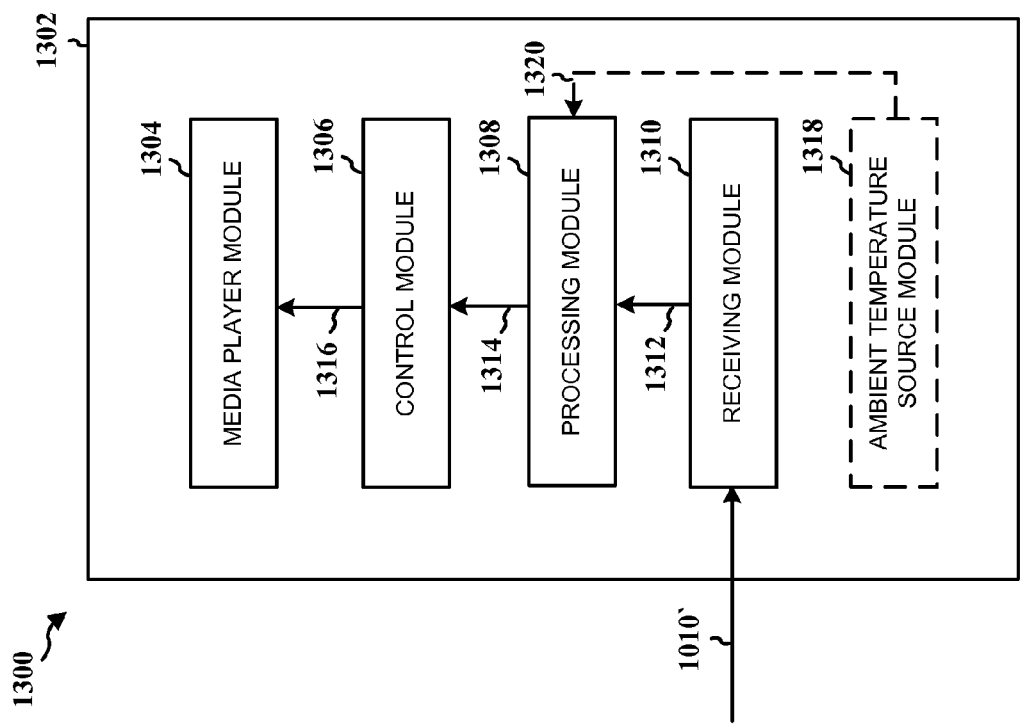
FIG. 13 is a conceptual data flow diagram illustrating the data flow between different modules/means/components in an apparatus corresponding to the first user device of FIG. 8.

FIG. 13 is a conceptual data flow diagram 1300 illustrating the data flow between different modules/means/components in an exemplary first-user-device apparatus 1302 configured to implement the process of the flow chart of FIG. 12. The apparatus 1302 may be a desktop computer, a laptop computer, a Smartphone, a MP3 player, or any other similar device having media player capability. The apparatus 1302 includes a media player module 1304 that plays audio and/or video content, a control module 1306 that controls operation of the media player 1304, a processing module 1308 that processes temperature signals, and a receiving module 1310 that receives temperature signals from a remote device. The apparatus 1302 may further include an ambient temperature source module 1318 that provides ambient temperature signals 1320 to the processing module 1308.

The apparatus may include additional modules that perform each of the steps of the algorithm in the aforementioned flow chart of FIG. 12, and the further details described with respect to those steps. As such, each step in the aforementioned flow chart of FIG. 12 may be performed by a module and the apparatus may include one or more of those modules. The modules may be one or more hardware components specifically configured to carry out the stated processes/algorithm, implemented by a processor configured to perform the stated processes/algorithm, stored within a computer-readable medium for implementation by a processor, or some combination thereof.

Figure 14:
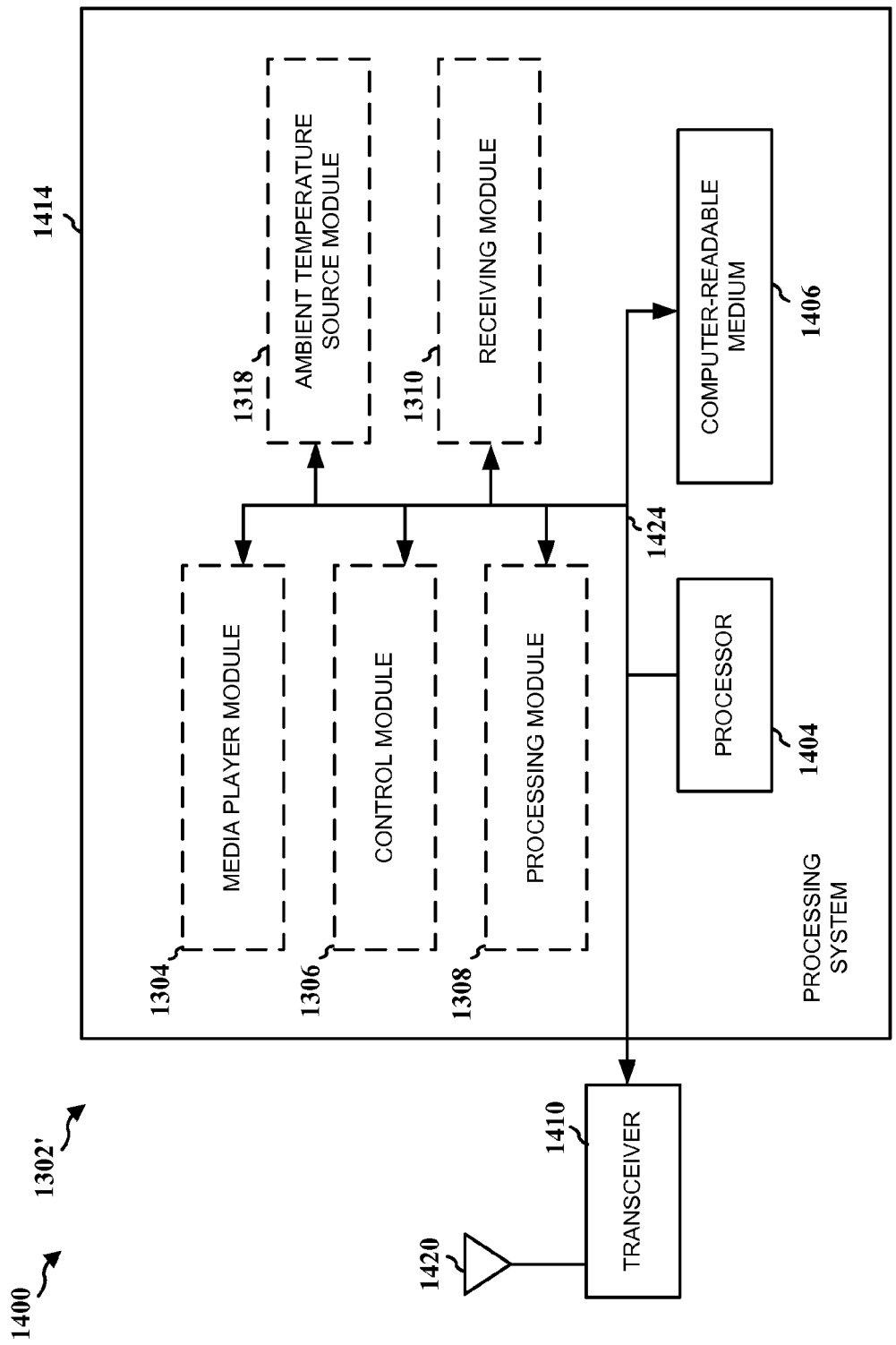
FIG. 14 is a diagram illustrating an example of a hardware implementation for an apparatus corresponding to the first user device of FIG. 8 employing a processing system.

FIG. 14 is a diagram 1400 illustrating an example of a hardware implementation for an apparatus 1302' employing a processing system 1414. The processing system 1414 may be implemented with bus architecture, represented generally by the bus 1424. The bus 1424 may include any number of interconnecting buses and bridges depending on the specific application of the processing system 1414 and the overall design constraints. The bus 1424 links together various circuits including one or more processors and/or hardware modules, represented by the processor 1404, the modules 1304, 1306, 1308, 1318 and the computer-readable medium 1406. The bus 1424 may also link various other circuits such as timing sources, peripherals, voltage regulators, and power management circuits, which are well known in the art, and therefore, will not be described any further.

The processing system 1414 may be coupled to a transceiver 1410. The transceiver 1410 is coupled to one or more antennas 1420. The transceiver 1410 provides a means for communicating with various other apparatus over a transmission medium. The transceiver 1410 receives a signal from the one or more antennas 1420, extracts information from the received signal, and provides the extracted information to the processing system 1414, specifically the receiving module 1308. The processing system 1414 includes a processor 1404 coupled to a computer-readable medium 1406. The processor 1404 is responsible for general processing, including the execution of software stored on the computer-readable medium 1406. The software, when executed by the processor 1404, causes the processing system 1414 to perform the various functions described supra for any particular apparatus. The computer-readable medium 1406 may also be used for storing data that is manipulated by the processor 1404 when executing software. The processing system further includes at least one of the modules 1304, 1306, 1308 and 1318. The modules may be software modules running in the processor 1404, resident/stored in the computer readable medium 1406, one or more hardware modules coupled to the processor 1404, or some combination thereof.

In one configuration, the apparatus 1302/1302' includes means for receiving a signal from a second user device remote from the first user device. The signal corresponds to a temperature sensed at the second user device. The apparatus 1302/1302' also includes means for processing the received signal relative to a temperature criterion, and means for initiating a control of the first user device if the criterion is satisfied. The aforementioned means may be one or more of the aforementioned modules of the apparatus 1302 and/or the processing system 1414 of the apparatus 1302' configured to perform the functions recited by the aforementioned means.

Figure 15:
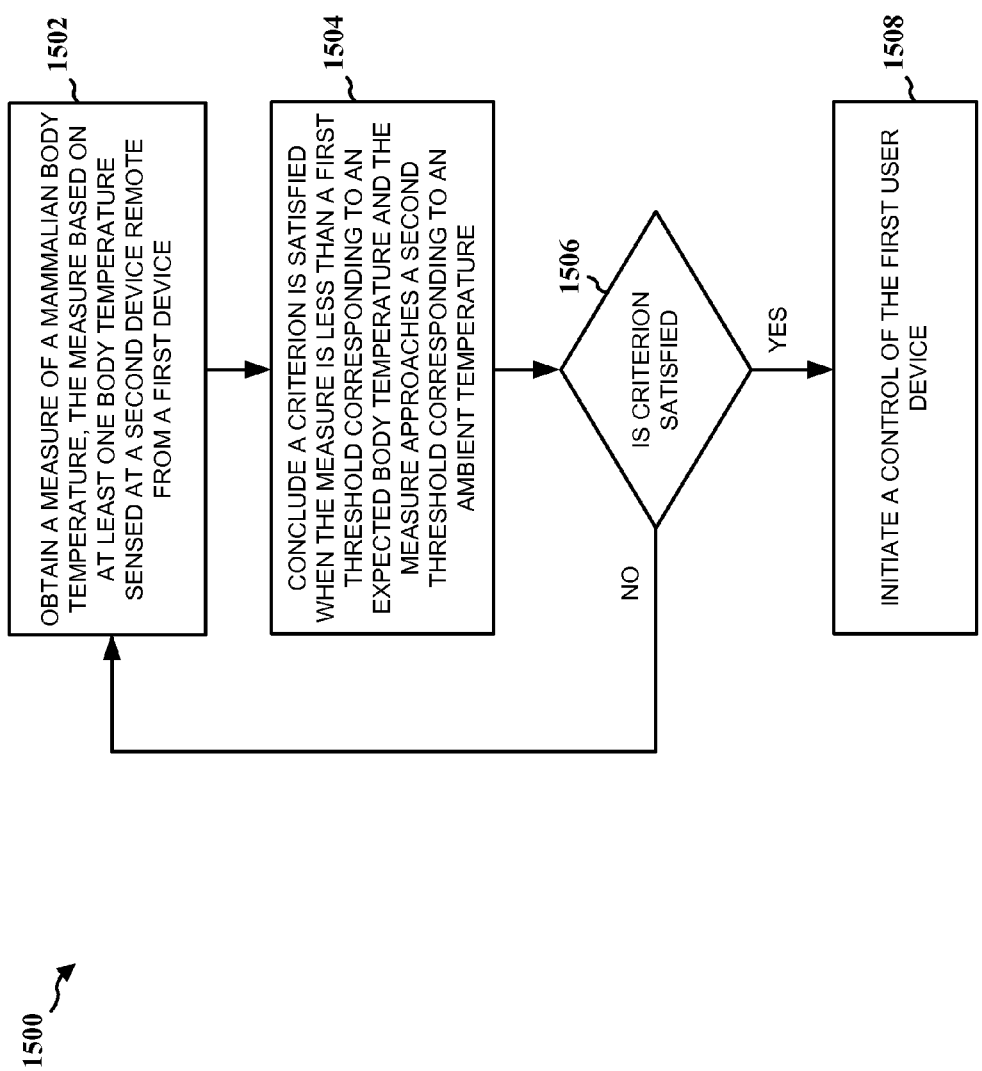
FIG. 15 is a flow chart of a temperature based method of initiating a control of a user device.

FIG. 15 is a flow chart of a method 1500 of controlling operation of a user device of FIGS. 1 and 8. The method 1500 may be performed by the first user device, such as the desktop computer, a laptop computer, a Smartphone, a MP3 player, or any other similar device having media player capability; a second user device, such as a such as earphones, headphone or glasses; or an apparatus/system including one or more elements from each of a first user device and a second user device.

At step 1502, a measure of a mammalian body temperature is obtained. The measure may be based on at least one body temperature sensed at a second device remote from a first device. At step 1504, a criterion is deemed satisfied when the measure is less than a first threshold corresponding to an expected body temperature and the measure approaches a second threshold corresponding to an ambient temperature. The processes of steps 1502 and 1504 may be similar to any one or more of the processes of steps 202 and 204 of FIG. 2, steps 502 and 504 of FIG. 5, steps 902 and 904 of FIG. 9, and steps 1202 and 1204 of FIG. 12, as described above. As such, the details of the processes of steps 1502 and 1504 are not repeated here. At step 1506, if the criterion is not satisfied, the process returns to step 1502. If the criterion is satisfied, then at step 1508, a control of the first user device is initiated.

One or more of the apparatuses illustrated in FIGS. 3, 6, 10 and 13, or components thereof, may be configured to implement the process of the flow chart of FIG. 15. In one configuration, an apparatus that implements the flow chart of FIG. 15 includes a module that obtains a measure of a mammalian body temperature, where the measure is based on at least one body temperature sensed at a second device remote from a first device. This module may correspond to a sensing module that senses body temperatures, such as those shown in FIGS. 3 and 10, or a receiving module that receives temperature measurements from another source, such as those shown in FIGS. 6 and 13. The apparatus that implements the flow chart of FIG. 15 also includes a module that concludes a criterion is satisfied when the measure is less than a first threshold corresponding to an expected body temperature and the measure approaches a second threshold corresponding to an ambient temperature. This module may correspond to a processing module, such as those shown in FIGS. 3 and 13. The apparatus that implements the flow chart of FIG. 15 further includes a module that initiates a control of the first user device when the criterion is satisfied. This module may correspond to a transmitting module that transmits a control signal to another device, such as those shown in FIGS. 3 and 10, or a control module that controls a device, such as those shown in FIGS. 6 and 13.

The apparatus may include additional modules that perform each of the steps of the algorithm in the aforementioned flow chart of FIG. 15, and the further details described with respect to those steps. As such, each step in the aforementioned flow chart of FIG. 15 may be performed by a module and the apparatus may include one or more of those modules. The modules may be one or more hardware components specifically configured to carry out the stated processes/algorithm, implemented by a processor configured to perform the stated processes/algorithm, stored within a computer-readable medium for implementation by a processor, or some combination thereof.

An apparatus that implements the flow chart of FIG. 15 may be embodied in a hardware implementation employing a processing system similar to those illustrated in FIGS. 4, 7, 11 and 14. In one configuration, a processing system that implements the flow chart of FIG. 15 includes a module that obtains a measure of a mammalian body temperature, where the measure is based on at least one body temperature sensed at a second device remote from a first device. This module may correspond to a sensing module, such as those shown in FIGS. 4 and 11, or a receiving module, such as those shown in FIGS. 7 and 14. The processing system that implements the flow chart of FIG. 15 also includes a module that concludes a criterion is satisfied when the measure is less than a first threshold corresponding to an expected body temperature and the measure approaches a second threshold corresponding to an ambient temperature. This module may correspond to a processing module, such as those shown in FIGS. 4 and 14. The processing system that implements the flow chart of FIG. 15 further includes a module that initiates a control of the first user device when the criterion is satisfied. This module may correspond to a transmitting module, such as those shown in FIGS. 4 and 11, or a control module, such as those shown in FIGS. 7 and 14. The operation of other components (e.g., bus, computer readable medium, etc.) of the processing system that implements the flow chart of FIG. 15, are as described above with respect to FIGS. 4, 7, 11 and 14.

In one configuration, an apparatus that implements the flow chart of FIG. 15 includes means for obtaining a measure of a mammalian body temperature, where the measure is based on at least one body temperature sensed at a second device remote from a first device. The apparatus also includes means for concluding a criterion is satisfied when the measure is less than a first threshold corresponding to an expected body temperature and the measure approaches a second threshold corresponding to an ambient temperature. The apparatus further includes means for initiating a control of the first user device when the criterion is satisfied. The aforementioned means may be one or more of the aforementioned modules of the apparatus that implements the flow chart of FIG. 15 and/or the processing system of the apparatus that implements the flow chart of FIG. 15 configured to perform the functions recited by the aforementioned means.

It is understood that the specific order or hierarchy of steps in the processes disclosed is an illustration of exemplary approaches. Based upon design preferences, it is understood that the specific order or hierarchy of steps in the processes may be rearranged. Further, some steps may be combined or omitted. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

What is claimed is:

1. A method comprising:
   obtaining a measure of a mammalian body temperature, the measure based on at least one body temperature sensed at a second user device remote from a first user device;
   concluding criteria defined by a first threshold temperature corresponding to an expected body temperature and a second threshold temperature obtained from an ambient temperature sensing source associated with an ambient environment are satisfied when the measure is less than the first threshold temperature and the measure approaches the second threshold temperature, wherein the measure approaches the second threshold temperature when the measure is within a predetermined range of the second threshold temperature, or when a rate of change of the measure exceeds a predetermined rate; and
   initiating a control of the first user device when the criteria are satisfied.

2. The method of claim 1, wherein the measure is obtained from a temperature sensor associated with the second user device.

3. The method of claim 1, wherein the measure corresponds to a single body temperature.

4. The method of claim 1, wherein the measure corresponds to a running average of a plurality of body temperatures sensed over a period of time.

5. The method of claim 1, wherein the measure corresponds to a combination of a plurality of body temperatures sensed from a plurality of temperature sensors.

6. The method of claim 1, wherein the ambient temperature sensing source is a temperature sensor associated with the first user device.

7. The method of claim 1, wherein the ambient temperature sensing source is a temperature sensor associated with the second user device.

8. The method of claim 1, wherein the ambient temperature sensing source obtains an ambient temperature independent of a temperature sensor associated with either of the first user device and the second user device.

9. The method of claim 1, wherein the second threshold temperature is provided by a first ambient temperature sensing source, and further comprising confirming the accuracy of the second threshold temperature based on a temperature provided by a second ambient temperature sensing source.

10. An apparatus comprising:
means for obtaining a measure of a mammalian body temperature, the measure based on at least one body temperature sensed at a second user device remote from a first user device;
means for concluding criteria defined by a first threshold temperature corresponding to an expected body temperature and a second threshold temperature obtained from an ambient temperature sensing source associated with an ambient environment are satisfied when the measure is less than the first threshold temperature and the measure approaches the second threshold temperature, wherein the measure approaches the second threshold temperature when the measure is within a predetermined range of the second threshold temperature, or when a rate of change of the measure exceeds a predetermined rate; and
means for initiating a control of the first user device when the criteria are satisfied.

11. The apparatus of claim 10, wherein the means for obtaining comprises a temperature sensor associated with the second user device.

12. The apparatus of claim 10, wherein the measure corresponds to a single body temperature.

13. The apparatus of claim 10, wherein the measure corresponds to a running average of a plurality of body temperatures sensed over a period of time.

14. The apparatus of claim 10, wherein the means for obtaining comprises a plurality of temperature sensors and the measure corresponds to a combination of a plurality of body temperatures sensed from the plurality of temperature sensors.

15. The apparatus of claim 10, wherein the ambient temperature sensing source is a temperature sensor associated with the first user device.

16. The apparatus of claim 10, wherein the ambient temperature sensing source is a temperature sensor associated with the second user device.

17. The apparatus of claim 10, wherein the ambient temperature sensing source comprises means for obtaining an ambient temperature independent of a temperature sensor associated with either of the first user device and the second user device.

18. The apparatus of claim 10, wherein the second threshold temperature is provided by the ambient temperature sensing source, and further comprising means for confirming the accuracy of the second threshold temperature based on a temperature provided by a second ambient temperature sensing source.

19. An apparatus comprising:
a memory; and
at least one processor coupled to the memory and configured to:
obtain a measure of a mammalian body temperature, the measure based on at least one body temperature sensed at a second user device remote from a first user device;
conclude criteria defined by a first threshold temperature corresponding to an expected body temperature and a second threshold temperature obtained from an ambient temperature sensing source associated with an ambient environment are satisfied when the measure is less than the first threshold temperature and the measure approaches the second threshold temperature, wherein the measure approaches the second threshold temperature when the measure is within a predetermined range of the second threshold temperature, or when a rate of change of the measure exceeds a predetermined rate; and
initiate a control of the first user device when the criteria are satisfied.

20. A non-transitory computer-readable medium storing computer executable code, comprising code to:
obtain a measure of a mammalian body temperature, the measure based on at least one body temperature sensed at a second user device remote from a first user device;
conclude criteria defined by a first threshold temperature corresponding to an expected body temperature and a second threshold temperature obtained from an ambient temperature sensing source associated with an ambient environment are satisfied when the measure is less than the first threshold temperature and the measure approaches the second threshold temperature, wherein the measure approaches the second threshold temperature when the measure is within a predetermined range of the second threshold temperature, or when a rate of change of the measure exceeds a predetermined rate; and
initiate a control of the first user device when the criteria are satisfied.

21. An apparatus, comprising:
a temperature sensor that obtains a measure of a mammalian body temperature; and
a processor that concludes criteria defined by a first threshold temperature corresponding to an expected body temperature and a second threshold temperature obtained from an ambient temperature sensing source associated with an ambient environment are satisfied when the measure is less than the first threshold temperature and the measure approaches the second threshold-temperature, wherein the measure approaches the second threshold temperature when the measure is within a predetermined range of the second threshold temperature, or when a rate of change of the measure exceeds a predetermined rate.

22. The apparatus of claim 21, further comprising the ambient temperature sensing source that provides the ambient temperature.

23. The apparatus of claim 21, wherein the ambient temperature sensing source comprises an ambient temperature sensor associated with an ambient environment.

24. The apparatus of claim 21, wherein the ambient temperature sensing source obtains an ambient temperature independent of a temperature sensor.

25. The apparatus of claim 21, further comprising a receiver that receives the ambient temperature from an ambient temperature sensing source remote from the apparatus.

26. The apparatus of claim 21, wherein the processor outputs a control signal when the criteria are satisfied, the control signal for initiating a control of a media player.

27. The apparatus of claim 26, further comprising a transmitter that transmits the control signal to the media player.

28. An apparatus, comprising:
a media player;
a receiver configured to receive a control signal when criteria defined by a first threshold temperature corresponding to an expected body temperature and a second threshold temperature obtained from an ambient temperature sensing source associated with an ambient environment are satisfied, the criteria being satisfied when a measure of a mammalian body temperature is less than the first threshold temperature and the measure approaches the second threshold temperature, wherein the measure approaches the second threshold temperature when the measure is within a predetermined range of the second threshold temperature, or when a rate of change of the measure exceeds a predetermined rate; and
a controller configured to control the media player in response to the control signal.

29. The apparatus of claim 28, further comprising the ambient temperature source that provides the ambient temperature.

30. The apparatus of claim 29, wherein the ambient temperature sensing source comprises an ambient temperature sensor associated with an ambient environment.

31. The apparatus of claim 29, wherein the ambient temperature sensing source obtains an ambient temperature independent of a temperature sensor.

32. An apparatus, comprising:
a receiver configured to receive a measure of a mammalian body temperature; and
a processor that concludes criteria defined by a first threshold temperature corresponding to an expected body temperature and a second threshold temperature obtained from an ambient temperature sensing source associated with an ambient environment are satisfied when the measure is less than the first threshold temperature and the measure approaches the second threshold temperature, wherein the measure approaches the second threshold temperature when the measure is within a predetermined range of the second threshold temperature, or when a rate of change of the measure exceeds a predetermined rate.

33. The apparatus of claim 32, further comprising the ambient temperature sensing source that provides the ambient temperature.

34. The apparatus of claim 33, wherein the ambient temperature sensing source comprises an ambient temperature sensor associated with an ambient environment.

35. The apparatus of claim 33, wherein the ambient temperature sensing source obtains an ambient temperature independent of a temperature sensor.

36. The apparatus of claim 32, further comprising a media player, wherein the processor outputs a control signal when the criteria are satisfied, the control signal for initiating a control of the media player.

* * * * *